United States Patent [19]
Bertone

[11] 4,127,024
[45] Nov. 28, 1978

[54] BATTERY VOLTAGE REGULATING AND CONDITION INDICATING CIRCUIT FOR MEASURING INSTRUMENTS

[75] Inventor: Gregory A. Bertone, Monroeville, Pa.

[73] Assignee: Mine Safety Appliances Company, Pittsburgh, Pa.

[21] Appl. No.: 797,334

[22] Filed: May 16, 1977

[51] Int. Cl.² .......................................... G01N 27/18
[52] U.S. Cl. ............................. 73/27 R; 324/65 R; 340/632
[58] Field of Search ...................... 73/27 R, 23, 204; 340/237 R, 248 B, 249; 23/254 E, 255 E; 324/65 R, DIG. 1

[56] References Cited

U.S. PATENT DOCUMENTS

| 3,478,579 | 11/1969 | Whitmore | 73/27 R |
|---|---|---|---|
| 3,482,233 | 12/1969 | Ogg | 73/27 R |
| 3,678,489 | 7/1972 | Scherban et al. | 73/27 R |
| 3,879,717 | 4/1975 | Gruensfelder | 340/249 |
| 4,007,456 | 2/1977 | Paige et al. | 340/248 B |

FOREIGN PATENT DOCUMENTS 826,780  11/1969  Canada .................................. 73/27 R Primary Examiner—Stephen A. Kreitman
Attorney, Agent, or Firm—Brown, Murray, Flick & Peckham

[57] ABSTRACT

A voltage regulating circuit is provided for low voltage battery-powered measuring instruments of the type using electrically-heated filaments as sensing elements. The circuit includes an indicating signal light which is energized from a separate control power source and controlled by the voltage regulating circuit and also in response to energization of a filament in the instrument. The light is turned OFF in case of failure of the control power or of inability of the voltage regulating circuit to maintain the desired voltage. The light is also turned OFF for a set time period upon energization of the filament to allow the filament to stabilize at its normal temperature. Thus, when the indicator light is ON an indication is provided that the instrument is in condition for use.

10 Claims, 1 Drawing Figure

U.S. Patent
Nov. 28, 1978
4,127,024
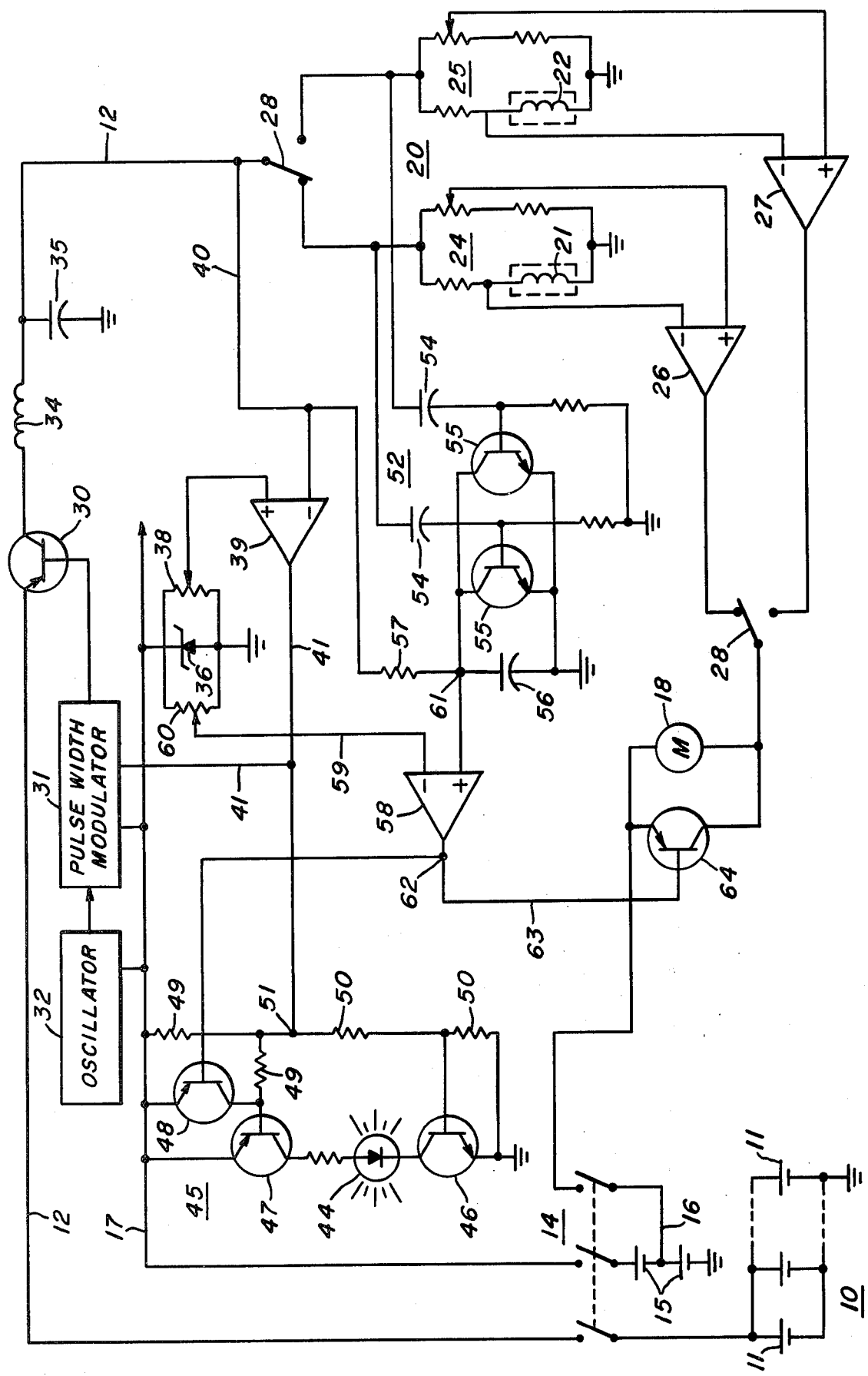

BATTERY VOLTAGE REGULATING AND CONDITION INDICATING CIRCUIT FOR MEASURING INSTRUMENTS

BACKGROUND OF THE INVENTION

The present invention relates to measuring instruments of the type using a heated filament or filaments as sensing means, and more particularly, to an accurately regulated battery voltage supply and circuit condition indicator for use in such instruments.

Instruments of this type use an electrically-heated filament for sensing purposes and observe changes in electrical resistance of the filament to measure such quantities as concentration of combustible gases flowing over the filament. The filament is usually connected in a bridge circuit so that the change in resistance is detected as a voltage which can be amplified and applied to a suitable meter. The meter can be calibrated to read the desired quantity directly. To obtain the desired accuracy, the voltage applied to such filaments for heating them to operating temperature must be held at an accurately determined constant value, so that the measured bridge voltage reflects only changes in resistance of the filament and is not affected by random or uncontrolled changes or fluctuations in the applied voltage. When such a filament is initially energized, a certain time is required for the filament to become heated and for its temperature to stabilize at the normal operating level. Readings taken during this time may be erroneous or inconsistent and means for preventing use of the meter during such periods, or for indicating that the meter is not capable of use, are very desirable.

SUMMARY OF THE INVENTION

The present invention provides a voltage regulating and condition indicating system for measuring instruments of the type using electrically-heated filaments, and especially for dual-range instruments of this type in which two different filaments are used alternatively for measurements in different ranges.

In accordance with the invention, such an instrument is provided with an accurately regulated, low-voltage battery power supply for the heated filaments, a high-frequency, pulse width modulated voltage regulator being utilized which is controlled by an error signal derived from the output voltage so as to maintain an extremely accurate voltage for supplying either of the two filaments. The filaments are connected in the usual manner in separate bridge circuits, and the resistance of each filament is determined by observing the diagonal voltage of its bridge which is amplified and applied to a meter which can be calibrated to read the desired quantity.

A separate source of control and auxiliary power is also provided, which may be another battery, and which supplies the necessary control power to the voltage regulator circuit, the amplifiers and other equipment. The condition of the circuit, that is, its availability for use at any given time, is shown by an indicating means which is preferably a visual signal such as a signal light directly energized from the control power source. The signal light is controlled by switching means to turn OFF at times when the circuit is not usable. Thus, time-delay means are provided associated with each of the filaments to turn the signal light OFF, and also to disable the meter, upon energization of either filament. After a set time-delay period sufficient to enable the filament to stabilize at its normal temperature, the light is turned ON and the meter restored to service. Switching means controlled in response to the error signal of the voltage regulator are also provided to turn OFF the indicating light whenever the voltage regulator is unable to maintain the regulated voltage because of low battery voltage, or for any other reason. Thus, the indicator light will be OFF for a predetermined time period whenever either filament is initially energized, and will be turned OFF whenever the voltage regulator is unable to maintain the desired voltage, or in case of failure of the control power supply. The indicator light is ON at other times to show that the system is capable of use, and is OFF under conditions which make the system inoperative or which could result in erroneous readings.

BRIEF DESCRIPTION OF THE DRAWING

The invention will be more fully understood from the following detailed description, taken in connection with the accompanying drawing, the single FIGURE of which is a schematic diagram showing an illustrative embodiment of the invention.

DESCRIPTION OF THE PREFERRED EMBODIMENT

The invention is shown in the drawing embodied in a battery power supply and condition indicating circuit for measuring instruments of the type described above. More particularly, the drawing shows a circuit for a dual-range, battery-operated, portable measuring instrument for measuring combustible gas concentrations. Such instruments employ two different heated filaments for measuring low gas concentrations and high gas concentrations, respectively. For measuring gas concentrations below a critical level, the gas mixture flowing over a hot platinum filament is catalytically burned on the surface of the filament, which raises the filament temperature and thus increases the electrical resistance of the filament. For gas mixtures with concentrations above the critical level, a thermal conductivity filament is used and the change in cooling effect due to differences between the thermal conductivity of the gas mixture and that of fresh air is detected as a temperature change in the filament which causes a change in its electrical resistance.

In both cases, the filaments are electrically heated to a nominal operating temperature, and an accurately controlled and constant voltage is required for this purpose so that apparent changes in resistance of the filament reflect only temperature changes due to the gas composition and not to fluctuations in the supply voltage. The filaments are connected to separate bridge circuits having constant resistances in the other legs of the bridge, so that the change in resistance of the filament is detected as a change in the voltage across the bridge which can be applied to a suitable meter calibrated to read the desired quantity. A selector switch may be used to switch the voltage supply and the meter from one filament to the other, and means must be provided for inhibiting any attempt to use the meter during the short period after initial energization of either filament which is necessary for it to heat up and become stabilized at the operating temperature. This, of course, may be done by disabling the instrument for the necessary time period, or by providing a suitable warning signal to indicate to the operator that no reading should be taken during that time.

The drawing shows an illustrative embodiment of a regulated battery voltage supply and indicating system for a dual-range instrument of the type discussed above. As there shown, the voltage supply source comprises a battery 10 consisting of a suitable number of cells 11, such as 1.5 volt battery cells of any suitable type, connected in parallel to a line 12 through a three-pole ON-OFF switch 14. A source of control and auxiliary power, which need not be accurately regulated, is also provided and may consist of two battery cells 15 connected in series to provide a three-volt source, with a center tap 16 between the cells. The control power source 15 is connected through a second pole of the switch 14 to a control power bus 17, and the center tap 16 is connected through the third pole of the switch 14 to an indicating meter 18.

The battery 10 supplies energizing voltage to a dual-range gas concentration measuring instrument 20 of the type described above. Such an instrument may have a platinum catalytic filament 21 for use in measuring gas concentrations below a critical level, and a thermal conductivity filament 22 for use with gas concentrations above the critical level. As previously described, each filament is electrically heated by the battery 10 and the voltage must be accurately regulated. The two filaments 21 and 22 are connected in identical bridge circuits 24 and 25, respectively, each consisting of constant resistances of suitable value connected as shown, with the filaments 21 and 22 as the only active legs of each bridge. The change in resistance of either filament, resulting from changes in concentration of the gas mixture flowing over it, thus appears as a change in the voltage across the diagonal of the bridge. In the illustrative embodiment, an operational amplifier 26 has its inputs connected across the diagonal of the bridge 24, while a similar amplifier 27 has its inputs connected across the diagonal of the bridge 25.

The regulated voltage appearing on the line 12 is selectively applied to either of the filaments 21 or 22, and the corresponding bridge 24 or 25, by means of one pole of a two-pole selector switch 28. The output of the corresponding amplifier 26 or 27 is similarly applied through the other pole of the switch 28 to the meter 18. The operational amplifiers 26 and 27 may be of any suitable or known type to amplify the voltages across the respective bridge circuits and to provide an output voltage signal representative of the change in bridge voltage as the temperature and resistance of the corresponding filament 21 or 22 change. Power for the amplifiers 26 and 27 may be provided from the control power bus 17, and any necessary feedback or other circuits may, of course, be provided, but these known circuits have not been shown to avoid unnecessary complication of the drawing. The meter 18 may be a milliammeter of any suitable type. The meter 18 has a substantially constant voltage applied from the battery tap 16 and a varying voltage from the amplifier 26 or 27, so that a current determined by the output voltage of the amplifier flows through the meter. Its reading, therefore, indicates the change in resistance of the corresponding filament 21 or 22 and, therefore, its temperature. The meter can be calibrated to read the desired gas concentration directly if desired.

As previously discussed, the voltage applied to the filaments 21 and 22 must be maintained as accurately constant as possible. In accordance with the present invention, the supply voltage is very low voltage, preferably a single battery cell voltage of 1.5 volts, so that standard battery cells can be used in a portable instrument. Even at this low voltage level, however, accurate regulation is very important and is an important feature of the invention. It has been found that the pulse width modulation type of voltage regulator can be used very effectively at low voltage levels and an accurate regulated output voltage of 1.000 volt can be maintained using a standard 1.5 volt battery cell as a power source. The voltage regulator itself may be of known type utilizing a transistor 30 as a power switch, although any suitable static switching device could be used. The power switch 30 is controlled by a pulse width modulator 31 of any suitable type driven by an oscillator 32 at a relatively high frequency such as 10 kilohertz, for example. The modulator 31 and oscillator 32 are energized from the control power bus 17, and operate to turn the switch 30 ON and OFF at the oscillator frequency and to control the width of the output pulses such as to maintain the average output voltage at the desired level. The output of the switch 30 is passed through a filter consisting of an inductor 34 and a shunt capacitor 35, and is applied through the selector switch 28 to either of the bridges 24 or 25 as previously described.

The pulse width modulator 31 is controlled to maintain the desired voltage by means of an error signal. The error signal is derived from a voltage reference which is obtained from a Zener diode 36 connected to the bus 17 as shown. A potentiometer 38 may be connected across the diode 36 to permit accurate adjustment of the desired voltage and the contact of the potentiometer 38 is connected to one input of an operational amplifier 39. The other input of the amplifier 39 is connected by a conductor 40 to the output voltage on the line 12. The amplifier 39 thus compares the reference voltage derived from the potentiometer 38 with the actual voltage on the conductor 40 and produces an error signal on the conductor 41 which is applied to the pulse width modulator 31 to control its operation. The operation of the amplifier 39 is such that a positive error signal voltage is obtained which varies slightly as required to control the point at which the switch 30 is turned OFF in each pulse to maintain the desired output voltage level. In this way, a very accurate regulated voltage is maintained for the instrument 20.

Indicating means are also provided to show positively and reliably that the instrument 20 is ready for use. This indication is provided by a visual signal device 44 which is preferably a light-emitting diode, although any other suitable visual signal such as a glow tube might be used. The indicator light 44 is directly energized from the control power bus 17 so that when it is lighted it indicates, among other things, that the control power source is operable. The indicator light 44 is controlled by a first switching means 45 and a second switching means 46 both of which are connected in series with the light 44. The first switching means 45 consists of a transistor 47 having its collector and emitter connected in series with the light 44, with a transistor 48 connected across the base and emitter of the transistor 47 to control its conduction. The base of transistor 47 is connected to the bus 17 through resistors 49 such that normally the base of transistor 47 is at a lower potential than the emitter, and since this transistor is of the PNP-type, it is conductive when the transistor 48 is turned OFF. The transistor 48 is normally OFF during operation but is controlled as described below to control the transistor 47.

The base of transistor 47 is also connected to the error signal conductor 41 at the point 51, as shown, and the base of transistor 46 is connected to the point 51 through a resistor 50. As previously described, the error signal which is present at point 51 is normally a small positive voltage. This error voltage varies as required to control the pulse width modulator 31, but is of proper magnitude to keep the transistors 46 and 47 conductive. When the voltage of the battery cells 11 falls to a level such that the regulator can no longer maintain the output voltage at the desired level, however, or if the system falls out of regulation for any other reason, the error signal at point 51 goes to a higher value and the transistor 47 is turned OFF so that the signal light 44 is deenergized.

The second switching means consists of transistor 46 which is of the NPN-type. The base of the transistor 46 is connected through resistors 49 and 50 to the control power bus 17. Transistor 46 is normally conductive but if the voltage of the bus 17 drops below a preset level determined by the resistors 49 and 50, the transistor 46 is turned OFF and the indicating light 44 is deenergized and goes out.

As discussed above, when one of the filaments 21 or 22 is energized, either when the instrument 20 is initially turned ON or when switching from one filament to the other, a certain time is necessary to allow the newly-energized filament to heat up and to stabilize at its operating temperature. The instrument should not be used during this time as any readings would be inaccurate and inconsistent. The indicating light 44 is, therefore, turned OFF during this period and the meter 18 is temporarily disabled. A time-delay circuit 52 is provided for this purpose. The time-delay circuit 52 includes two branches, one for each of the bridges 24 and 25, each branch consisting of a capacitor 54 connected to control a transistor 55 and connected to be energized from the line 12 by the switch 28. The two transistors 55 are connected in parallel across a capacitor 56 which is connected to be charged through a resistor 57 from the constant output voltage on the conductor 40. The capacitor 56 is connected to one input of an operational amplifier 58 and the other input of the amplifier 58 is connected to a fixed voltage obtained through conductor 59 from a tap on a resistor 60 connected across the voltage reference diode 36.

In the operation of this time-delay circuit, when either filament 21 or 22 is energized, by the switch 28, the corresponding capacitor 54 is connected to the line 12 and a charging current flows to the capacitor. During the brief duration of this charging current, the base of the corresponding transistor 55 is at a high enough potential to make the transistor conductive, which allows the capacitor 56 to discharge rapidly. When the charging current ceases to flow, the base of the transistor 55 is at ground potential and the transistor ceases to conduct. The capacitor 56 then charges from the voltage of the line 12 at a rate determined by the resistor 57. While capacitor 56 is charging, the point 61 is at or close to ground potential and the output of the operational amplifier 58 at point 62 is at a low level. After a time period which may be of the order of four seconds, for example, the capacitor 56 is fully charged and the charging current falls to zero. The potential of the point 61 is then essentially the voltage of line 12 and the output of amplifier 58 at point 62 rises to a substantially higher level.

The output of the amplifier 58 at point 62 is applied to the base of transistor 48 which is part of the first switching means for the indicator light as previously described. The amplifier output at point 62 is also applied through a conductor 63 to the base of a PNP transistor 64 connected across the meter 18. Since a low or even negative potential is thus applied to the bases of transistors 48 and 64 during the time-delay period of the circuit 52, both transistors are conductive for this time period. Transistor 47 is, therefore, turned OFF, as its base and emitter are shorted together, and the indicator light 44 is turned OFF. At the same time, the meter 18 is shunted by the transistor 64 so that the meter is disabled and its reading goes to zero. After the delay period has elapsed and the output of amplifier 58 goes to its normal high positive value, transistors 48 and 64 turn OFF so that the indicator light is turned ON and the shunt is removed from the meter 18 to restore it to service. The instrument 20 is then ready for normal use.

It will now be seen that a regulated battery voltage supply and condition indicating system has been provided for dual-range meters of the heated filament type, although it can equally well be used with a single filament. The system provides a highly accurate regulated voltage for energizing the filaments even at the low voltage level of a standard battery cell suitable for portable meters. The indicating means provides a reliable indication showing when the instrument is in condition for use. That is, the indicator light is normally ON but is turned OFF for a fixed time period upon energization of either of the filaments either when the instrument is initially turned ON by the switch 14 or when switching from one filament to the other. In either case, the light goes OFF indicating that the instrument is not capable of use and the meter 18 is simultaneously disabled. After the time period has elapsed, the light turns ON and the meter is restored to service indicating that the instrument can now be used. In addition, the indicator light is turned OFF if the system goes out of regulation showing that the battery voltage has fallen too low, or that for some other reason the regulator cannot maintain the desired voltage. The light also goes OFF if the control power supply voltage drops below a set level for any reason. Thus, a very desirable system is provided for instruments using a heated filament or filaments which maintains an accurate regulated voltage for the filaments and provides a reliable indication of the condition of the system which shows when it is in condition for use.

I claim as my invention:

1. In combination, a measuring instrument including an electrically-heated filament, means for measuring the resistance of said filament, a meter connectible to said measuring means, a battery connectible to the filament, voltage regulating means for controlling the output of said battery to supply an accurately regulated voltage to the filament, and indicator means for indicating when said instrument is in condition for use, said indicator means including a single signal means and means for controlling said signal means to indicate the occurrence of any of a plurality of conditions under which the instrument is not usable, said signal means being a normally energized visual signal, and means for turning OFF said visual signal when the voltage supplied to said filament is below the normal regulated voltage.

2. The combination of claim 1 in which said voltage regulating means includes a power switch, a pulse width modulator for controlling said switch, and means responsive to the output voltage of the switch for generating an error signal to control said pulse width modulator.

3. The combination of claim 2 in which the indicator means includes, switch means for said visual signal, and means for controlling said last-mentioned switch means in response to the error signal to turn OFF the visual signal when the voltage supplied to said filament is below the normal regulated voltage.

4. The combination of claim 1 including time-delay means operable upon energization of the filament, and means controlled by said time-delay means for turning OFF said visual signal for a predetermined time period.

5. The combination of claim 4 and including means controlled by said time-delay means for short-circuiting said meter.

6. The combination of claim 1 including an independent power source for supplying control power, said visual signal being connected to said power source to be directly energized thereby, means for deenergizing the visual signal when the voltage supplied to said filament is below the normal regulated voltage, and time delay means for deenergizing the visual signal for a predetermined time period upon energization of said filament.

7. The combination of claim 6 and including means controlled by said time-delay means for disabling said meter during said time period.

8. The combination of claim 7 and including first and second switching means for controlling energization of said visual signal, means controlled by said voltage regulator for actuating said first switching means to deenergize the visual signal when the voltage supplied to said filament is below the normal regulated voltage, means controlled by said time-delay means for actuating said first switching means to deenergize the visual signal for said predetermined time period, and means for actuating said second switching means to deenergize the visual signal when the voltage of said control power source falls below a predetermined value.

9. The combination of claim 1 in which said instrument is a dual-range instrument having an electrically-heated filament for each range, and means for selectively connecting said meter and said battery to either filament.

10. The combination of claim 9 including a visual signal, means for normally continuously energizing said visual signal, means for turning OFF said signal when the voltage supplied to said filaments is below the normal regulated voltage, and means for turning OFF the signal for a predetermined time period upon energization of either filament.

* * * * *